(12) United States Patent
Kawai et al.

(10) Patent No.: US 7,887,640 B2
(45) Date of Patent: Feb. 15, 2011

(54) MEDICAL MANIPULATOR AND CLEANING METHOD FOR MEDICAL MANIPULATOR

(75) Inventors: Junko Kawai, Shibuya-ku (JP); Shuji Imuta, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 269 days.

(21) Appl. No.: 12/175,577

(22) Filed: Jul. 18, 2008

(65) Prior Publication Data
US 2009/0030449 A1 Jan. 29, 2009

(30) Foreign Application Priority Data
Jul. 25, 2007 (JP) ............................... 2007-193526

(51) Int. Cl.
*B08B 9/035* (2006.01)
*B08B 5/04* (2006.01)
*B08B 3/04* (2006.01)
(52) U.S. Cl. .................. 134/22.12; 134/21; 134/34; 600/133; 600/136
(58) Field of Classification Search ............. 134/21, 134/22.12, 34; 600/127, 133
See application file for complete search history.

(56) References Cited
U.S. PATENT DOCUMENTS
6,331,181 B1 12/2001 Tierney et al.
7,314,473 B2 1/2008 Jinno et al.

2008/0039255 A1 2/2008 Jinno et al.
2010/0076483 A1 3/2010 Imuta

FOREIGN PATENT DOCUMENTS
JP 10309263 A * 11/1998
JP 2004-105451 4/2004
JP 2008-36793 2/2008

OTHER PUBLICATIONS
Yukio Takahashi, machine translation of JP 10-309263A, Nov. 1998.*

* cited by examiner

*Primary Examiner*—Michael Kornakov
*Assistant Examiner*—Natasha Campbell
(74) *Attorney, Agent, or Firm*—Oblon, Spivak, McClelland, Maier & Neustadt, L.L.P.

(57) ABSTRACT

A medical manipulator and a cleaning method therefor are provided. The medical manipulator includes an operation command unit equipped with a motor, and a working unit, which is detachable with respect to the operation command unit. A connector of the working unit is connected to the operation command unit, and includes pulleys that engage with the motor, the connector serving to rotatably retain the pulleys therein. The connector has an elongate shape extending in the longitudinal direction of a connecting shaft, and a first cleaning hole is arranged in an end portion of the connector that is opposite to a side on which the connecting shaft is connected. A second cleaning hole opens into an interior cavity, in the vicinity of an end portion on the side where the connecting shaft is connected. The end portions are shaped substantially hemispherically.

3 Claims, 16 Drawing Sheets

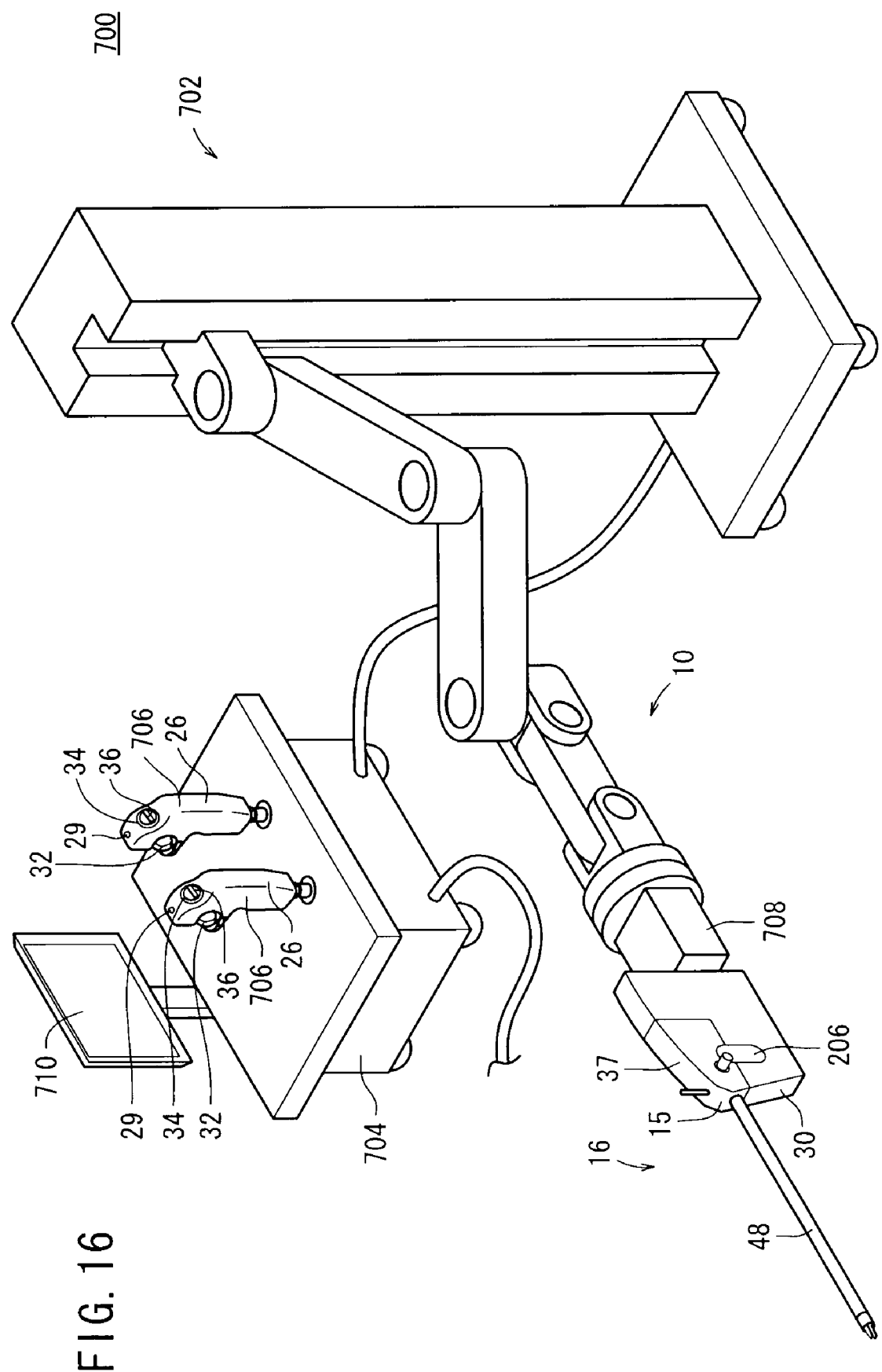

MEDICAL MANIPULATOR AND CLEANING METHOD FOR MEDICAL MANIPULATOR

BACKGROUND OF THE INVENTION

1. Field of the Invention

The present invention relates to a medical manipulator and a cleaning method therefor, and in particular, concerns a medical manipulator equipped with a drive unit and a working unit, which is detachable with respect to the drive unit, as well as a cleaning method for such a medical manipulator, which can favorably be applied to the working unit of the medical manipulator.

2. Description of the Related Art

In laparoscopic surgery, a number of small holes are opened in a patient's abdomen or the like, and an endoscope, forceps (or manipulators) or the like is inserted into such holes, and surgery is carried out while the surgeon observes an image from the endoscope on a display monitor. In this type of laparoscopic surgery, because opening of the abdominal cavity is not required, the burden on the patient is small, and the number of days required for the post-operative recovery and the number of days spent in the hospital can be significantly reduced. Therefore, laparoscopic surgical operations are expected to find an increased range of applications.

A manipulator system, for example, as disclosed in Japanese Laid-Open Patent Publication No. 2004-105451, comprises a manipulator main body, and a controller for controlling the main body. The manipulator main body comprises an operation command unit, which is operable by hand, and a working unit, which is detachable and exchangeable with respect to the operation command unit.

The working unit (tool) includes an elongate connecting shaft, and a distal end working unit (also referred to as an "end effector") disposed at the end of the connecting shaft. One or more actuators (motors) are disposed in an operation command unit for driving the working unit by means of wires. The wires are wound around pulleys at a proximal end side. The controller drives the motors disposed in the operation command unit, and also drives the wires in an advancing/retracting manner via the pulleys.

The working unit is constructed so as to be detachable with respect to the operation command unit in order to enable cleaning to be carried out easily following completion of a surgical technique. Further, in laparoscopic surgery, various different types of working units are used depending on the surgery involved. A gripper, scissors, an electrical knife, an ultrasonic knife, a surgical drill or the like may be given as examples thereof. From the standpoint of being able to exchange these working units, a structure in which the working unit is detachable with respect to the operation command unit also is beneficial.

In the working unit, proximal end side pulleys thereof are constructed so as to engage with the rotational shafts of motors, which are disposed in the operation command unit.

By detaching and removing the working unit from the operation command unit, cleaning processing performed on the working unit becomes considerably easier. However, it would also be desirable for cleaning of a retaining chamber, which rotatably supports and retains the driven rotating bodies that engage with rotating actuators, to be conducted more easily.

Further, The pulleys and gears are connected by wires within the working unit, whereby motive forces are transmitted thereby. It is desired to easily and reliably transmit motive forces through such pulleys, gears, and wires.

SUMMARY OF THE INVENTION

It is an object of the present invention to provide a medical manipulator having a more suitable working unit, in which a working mechanism can be suitably applied with respect to the working unit or the like of the medical manipulator, as well as to provide a cleaning method for such a working mechanism.

According to one aspect of the present invention, the medical manipulator includes a drive unit equipped with a rotary actuator, and a working unit which is detachable with respect to the drive unit, the working unit comprising a distal end working unit which is operatively coupled to the rotary actuator, wherein the working unit further comprises a driven rotating body engaged with the rotary actuator at a connection location of the drive unit, a retaining chamber for rotatably supporting and retaining the driven rotating body, and at least two cleaning holes through which a cleaning agent is made to flow into and through the retaining chamber, wherein the working unit includes a connecting shaft interconnecting the retaining chamber and the distal end working unit, the retaining chamber has an elongate shape extending in the longitudinal direction of the connecting shaft, the driven rotating body comprises a plurality of driven rotating bodies arrayed in parallel along a longitudinal direction of the retaining chamber, and at least one of the cleaning holes is disposed on a side opposite from a side on which the connecting shaft is connected, and is disposed at a position shifted from a parallel axis of the driven rotating bodies.

By causing the cleaning agent to flow through the retaining chamber from at least two cleaning holes, the interior cavity of the retaining chamber and the driven rotating bodies can easily be cleaned. Due to the fact that at least one of the cleaning holes is disposed on a side opposite from a side on which the connecting shaft is connected, and is disposed at a position shifted from a parallel axis of the driven rotating bodies, the cleaning agent, which flows in through the cleaning holes, is rotated while flowing through the interior of the retaining chamber, whereby the cleaning effect performed thereby is enhanced.

When the retaining chamber has an elongate shape, and both ends of the interior cavity of the retaining chamber in the longitudinal direction thereof are substantially hemispherically shaped, it is difficult for foreign matter to accumulate inside of the interior cavity.

When ends of the driven rotating bodies in the retaining chamber expand in diameter in directions toward respective walls of the retaining chamber, it also is difficult for foreign matter to collect and accumulate on the ends of the driven rotating bodies.

According to another aspect of the present invention, there is provided a cleaning method for a medical manipulator, in which the medical manipulator includes a drive unit equipped with a rotary actuator, and a working unit which is detachable with respect to the drive unit, the working unit having a distal end working unit which is operatively connected to the rotary actuator, and wherein the working unit further includes a driven rotating body engaged with the rotary actuator at a connection location of the drive unit, a retaining chamber for rotatably supporting and retaining the driven rotating body, and at least one cleaning hole through which a cleaning agent is made to flow into and through the retaining chamber, the cleaning method includes the steps of detaching the working unit from the drive unit, connecting and sealing the cleaning hole to one end of a tube, providing a cleaning agent suction and discharge means on another end of the tube, immersing an end of a shaft of the medical manipulator into the cleaning agent, and operating the suction and discharge means to repeatedly carry out sucking and discharging of the cleaning agent from the end of the shaft, and thereby causing the cleaning agent to flow through the retaining chamber.

In accordance with the above method, the cleaning agent can be sucked into and discharged from the interior cavity through a hollow space inside the shaft, so that both the shaft and the retaining chamber can be cleaned easily at the same time.

Still further, according to another aspect of the present invention, the medical manipulator includes a drive unit equipped with a rotary actuator and a working unit which is detachable with respect to the drive unit, the working unit comprising a distal end working unit which is operatively coupled to the rotary actuator, the medical manipulator further comprising a wire coupled to and being advanced and retracted by the rotary actuator, a rotating body around which the wire is wound and which is coupled to the distal end working unit, a recess disposed in a side wall of the rotating body and which is formed more narrowly toward a deeper region thereof, and a fixing member that covers the wire from a side thereof, and a portion of which is inserted into the recess for fixing the wire thereto, wherein, as viewed in cross section, the fixing member surrounds three sides of the wire, wherein both end pieces of the fixing member project from an surface of the wire, and wherein the both end pieces approach each other by inserting both end pieces into the recess, thereby pressing and fixing the wire.

In this manner, as a result of both end pieces of the fixing member being inserted into the recess of the rotating body, whereby the both end pieces approach each other and the wire is pressed and fixed, the wire can easily and reliably be affixed with respect to the rotating body.

According to another aspect of the present invention, the medical manipulator further is characterized by a drive unit equipped with a rotary actuator, and a working unit which is detachable with respect to the drive unit, the working unit having a distal end working unit which is operatively coupled to the rotary actuator, the medical manipulator further comprising a wire coupled to and being advanced and retracted by the rotary actuator, a rotating body around which the wire is wound and which is coupled to the distal end working unit, a cylindrical recess having a constant diameter disposed in a side surface of the rotating body, and a fixing member having a through hole through which the wire is inserted, a portion of the fixing member being inserted into the cylindrical recess for fixing the wire, wherein the fixing member 124 is affixed with respect to the rotating body and the wire by means of welding.

In the above manner, by providing a cylindrical recess having a constant diameter disposed in the rotating body, and further by utilizing the fixing member, which is fitted into the recess, proper positioning of the wire with respect to the rotating body is assured.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 16 is an outline perspective view of a surgical robot system in which the working unit is connected to an end of a robot arm.

DESCRIPTION OF THE PREFERRED EMBODIMENTS

Embodiments of a medical manipulator and a cleaning method for such a medical manipulator according to the present invention shall be explained below while referring to FIGS. 1 through 16.

The medical manipulator 10 grips a portion of a living body or a curved needle or the like by a distal end working unit 12 to carry out predetermined processing, and ordinarily is referred to as a gripping forceps or a needle driver (needle forceps) or the like.

Figure 1:
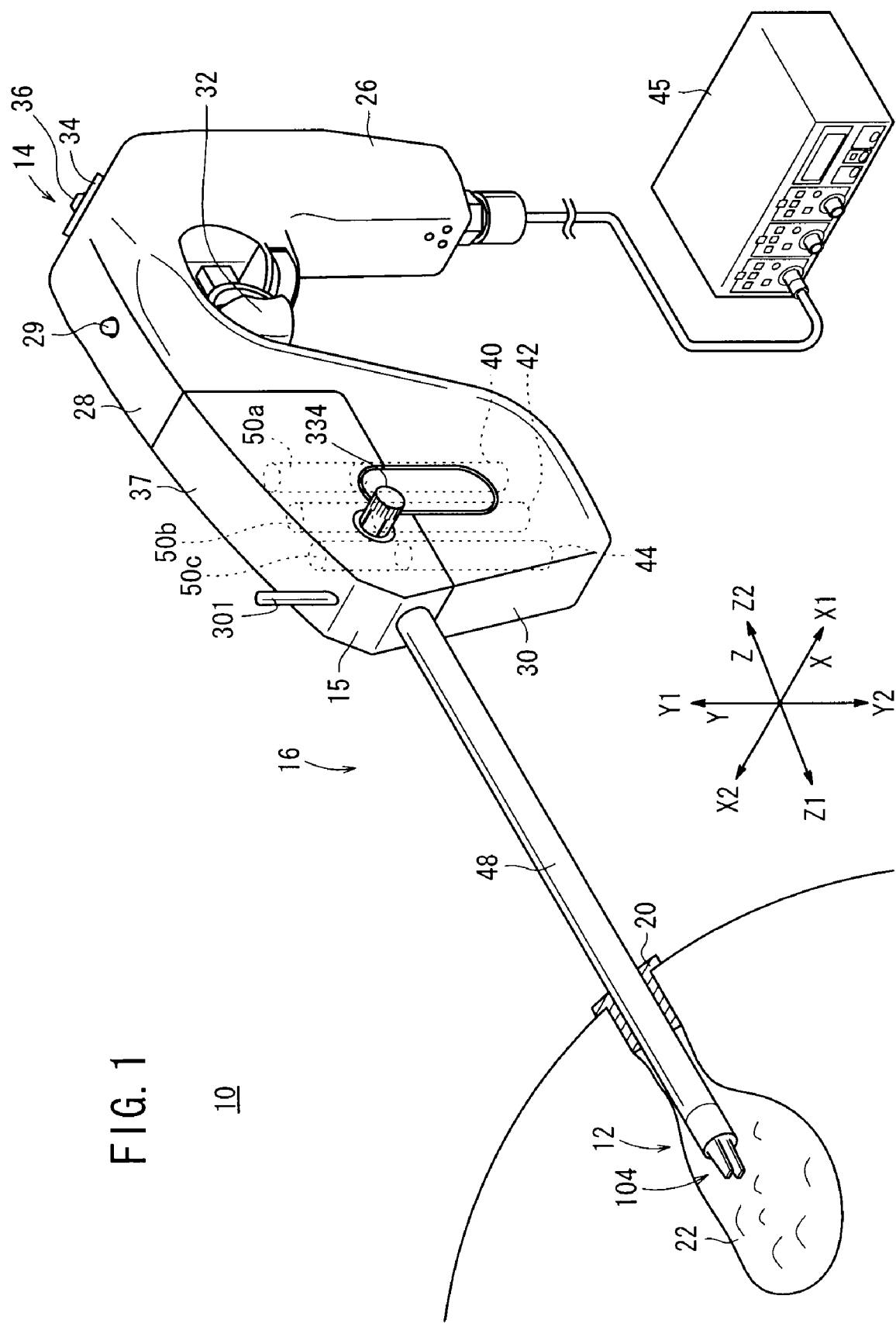
FIG. 1 is a perspective view of a manipulator according to an embodiment of the present invention.
Figure 2:
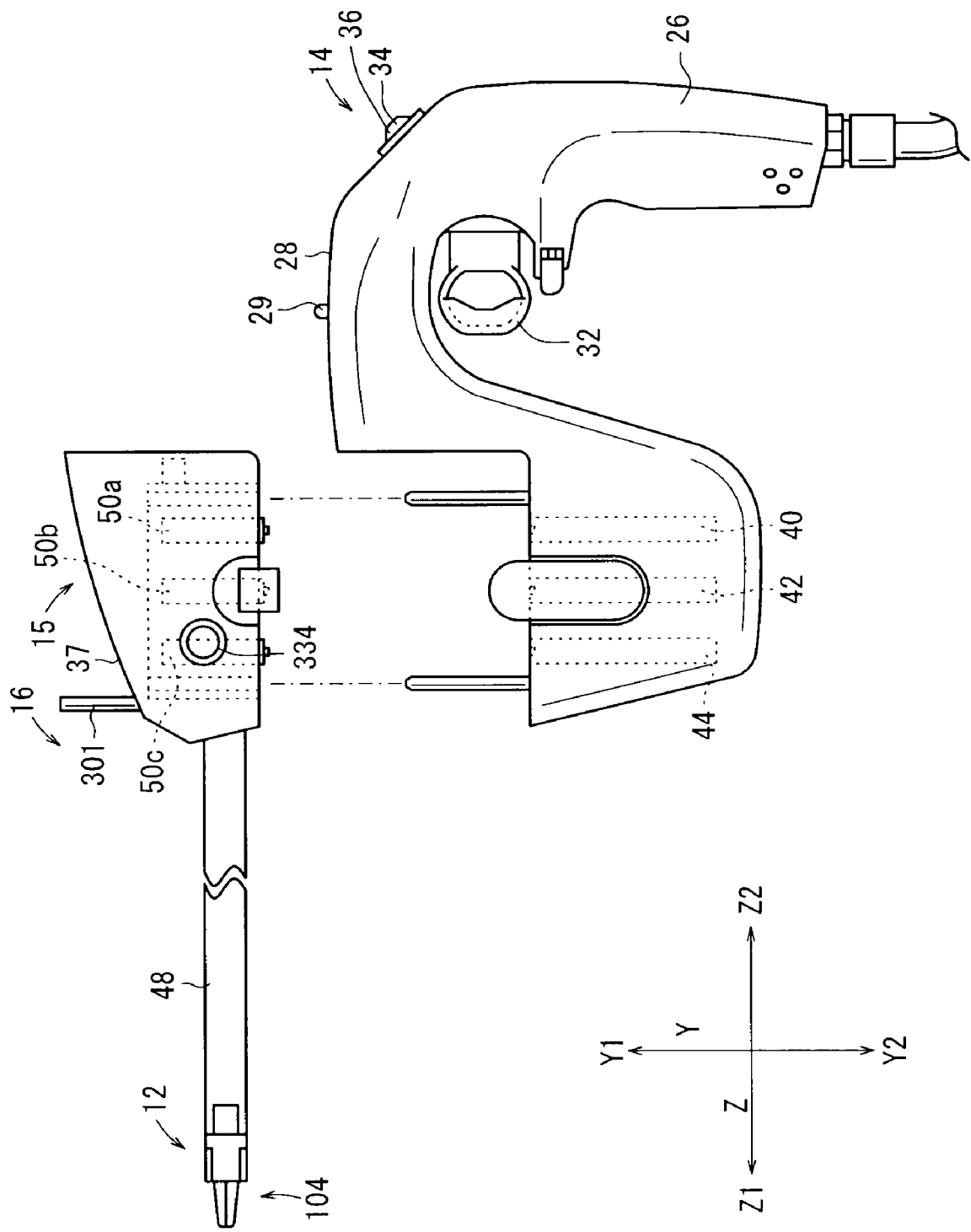
FIG. 2 is a side plan view of the manipulator, in which a working unit and an operation command unit thereof are separated from each other.

As shown in FIGS. 1 and 2, the manipulator 10 includes an operation command unit (drive unit) 14 of a proximal end portion thereof, which is gripped and operated by hand, and a working unit 16, which is attachable and detachable with respect to the operation command unit 14.

It shall be assumed in the following descriptions that, as shown in FIG. 1, the transverse direction is defined as an X direction, the vertical direction as a Y direction, and the longitudinal directions of the connecting shaft 48 as a Z direction. Further, among the X directions, the rightward direction is defined as an X1 direction, and the leftward direction as an X2 direction, among the Y directions, the upward direction is defined as a Y1 direction, and the downward direction as a Y2 direction, and among the Z directions, the forward direction is defined as a Z1 direction, and the rearward direction as a Z2 direction. Moreover, unless otherwise noted, these directions represent directions of the manipulator 10 when it is in a neutral posture (the posture of the state shown in FIG. 3). The definitions of the above directions are for illustrative purposes only, and the manipulator 10 can be used in any of various orientations (for example, the manipulator may be used upside down).

The working unit 16 includes a distal end working unit 12, a connector (retaining chamber) 15 that is connected to an actuator block 30 of the operation command unit 14, and a hollow connecting shaft 48 of a given length dimension connected between the distal end working unit 12 and the connector 15. The working unit 16 is capable of being detached and separated from the operation command unit 14 by means of a predetermined operation in the actuator block 30, wherein cleaning, disinfecting or sterilizing, maintenance and the like can be carried out thereon. The construction and manner of using the connector 15 will be discussed subsequently.

The distal end working unit 12 and the connecting shaft 48 are narrow in diameter, and can be inserted into a body cavity 22 through a trocar 20 in the form of a hollow cylinder mounted in an abdominal region or the like of the patient. By operations of the operation command unit 14, various techniques can be performed to cut, grip, remove, suture, or ligate (tie-knot) an affected part of the patient's body within the body cavity 22.

The operation command unit 14 includes a grip handle 26 gripped by hand, a bridge 28 extending from an upper portion of the grip handle 26, and an actuator block 30 connected to a distal end of the bridge 28.

As understood clearly from FIG. 1, a lower surface of the connector 15 abuts against an upper surface of the actuator block 30 with substantially no gaps therebetween, whereas the rear surface (surface facing the Z2 direction) of the connector 15 abuts against a front surface (surface facing the Z1 direction) of the bridge 28 with substantially no gaps therebetween. The lower surface of the connector 15 and the upper surface of the actuator block 30 lie in the XZ plane, and the rear surface of the connector 15 and the front surface of the bridge 28 lie in the XY plane. The left and right side surfaces of the connector 15 and the left and right side surfaces of the bridge 28 and the actuator block 30 make up a continuous YZ plane respectively, whereas the upper surface of the connector 15 and the upper surface of the bridge 28 respectively and continuously form a smooth curved surface. Owing thereto, in terms of design, the connector 15 is formed integrally and compactly with respect to the operation command unit 14, and moreover, since unnecessary irregularities in shape hardly exist at the region where the connector 15 and the operation command unit 14 are interconnected, operability is excellent.

The grip handle 26 includes a trigger lever 32, which is operable by a finger of the user, a first command lever 34, and a second command lever 36. The trigger lever 32 is disposed in a position where it can easily be pulled by the index finger.

The actuator block 30 houses therein three motors 40, 42, 44 (actuators) corresponding to respective mechanisms providing three degrees of freedom, which are incorporated in the distal end working unit 12. The motors 40, 42, 44 are arrayed in parallel in the longitudinal direction of the connecting shaft 48. The motors 40, 42, 44 are small in size and narrow in diameter, thereby allowing the actuator block 30 to have a compact flat shape. The actuator block 30 is disposed downwardly of the end of the operation command unit 14 in the Z1 direction. The motors 40, 42, 44 can be energized to rotate drive shafts thereof under the control of a controller (control unit) 45, based on operations of the operation command unit 14.

The connector 15 is covered by a resin cover 37, and houses and retains rotatably therein driven pulleys (driven rotating bodies) 50*a*, 50*b*, 50*c*, which engage with drive axes of the motors 40, 42, 44. Wires (linear bodies) 52, 54, 56 are wound respectively around pulleys 50*a*, 50*b*, 50*c*, extending to the distal end working unit 12 through a hollow space 48*a* (see FIG. 3) of the connecting shaft 48. The wires 52, 54, 56 can be formed, of the same type of materials having the same diameter, respectively.

The wires 52, 54, 56 serve to transmit motive forces to a compound mechanism 102 and the end effector 104 through a wire coupling 100 (see FIG. 3) at the end of the connecting shaft 48.

Further, between the cover 160 and the connecting shaft 48, a gap 51 is provided through which a gear 134, and another gear 138, etc., are exposed. The gap 51 communicates with the hollow space 48*a* of the connecting shaft 48.

A pair of tongue-members 58, which project at the distal end of the connecting shaft 48, are disposed so as to face one another toward the central axis of the connecting shaft 48. The hollow space 48*a* of the connecting shaft 48 communicates with the space formed between the pair of tongue-members 58. Two pairs of respective shaft holes 60*a*, 60*a* and 60*b*, 60*b* are disposed in confronting positions in the pair of tongue-members 58. The distal ends of the tongue-members 58 are formed with arcuate shapes, respectively.

The two shaft holes 60*a*, 60*a* and the two shaft holes 60*b*, 60*b* are disposed so as to sandwich the central axis therebetween. The shaft holes 60*a* and 60*b* are disposed in parallel along the Z direction, with the shaft holes 60*b* being positioned more closely to the distal end side than the shaft holes 60*a*.

Figure 3:
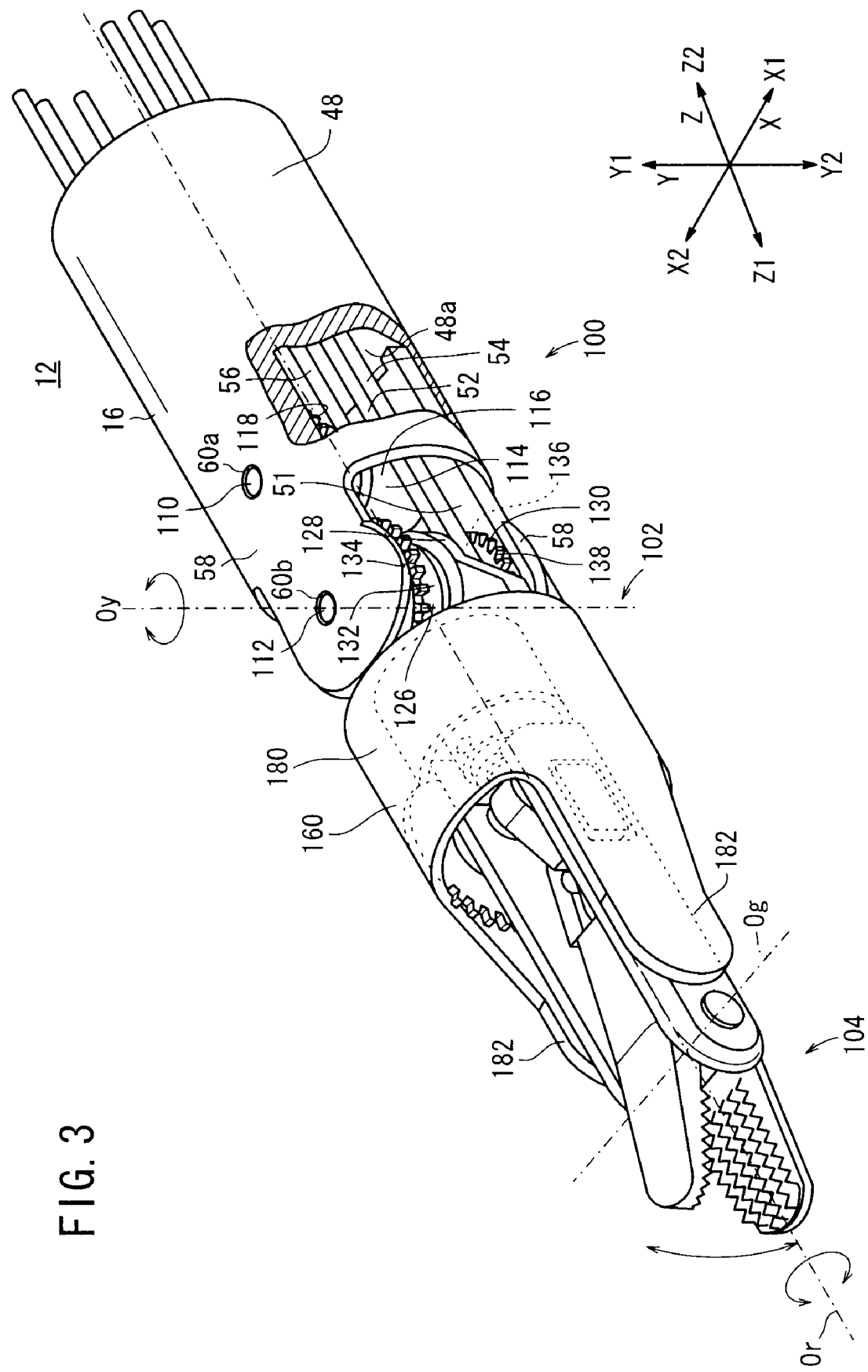
FIG. 3 is a perspective view of a working unit in the manipulator according to the present embodiment.

As shown in FIG. 3, the distal end working unit 12 incorporates therein mechanisms providing three degrees of freedom. These mechanisms include a mechanism having a first degree of freedom for rotating an end portion that is positioned ahead of a first rotational axis Oy (pivot axis) extending along the Y-axis direction, in yawing directions about the first rotational axis Oy, a mechanism having a second degree of freedom for rotating the end portion in rolling directions about a second rotational axis Or, and a mechanism having a third degree of freedom for opening and closing the end effector 104 about a third rotational axis Og.

The end effector 104 makes up a portion for performing actual work during an operation. The first rotational axis Oy and the second rotational axis Or serve to change the posture of the end effector 104 to facilitate working. In general, the mechanism having the third degree of freedom for opening and closing the end effector 104 is referred to as a gripper. The mechanism having the first degree of freedom for rotating in yawing directions is referred to as the yaw axis, whereas the mechanism having the second degree of freedom for rotating in rolling directions is referred to as the roll axis.

The distal end working unit 12 is made up of and includes the wire coupling 100, the compound mechanism 102, and the end effector 104.

With reference to FIG. 3, detailed explanations shall now be made concerning the wire coupling 100, the compound mechanism 102, and the end effector 104.

The wire coupling 100 is disposed between the pair of tongue-members 58, and serves to convert reciprocating motions of the respective wires 52, 54, 56 into rotary motions, which are then transmitted to the compound mechanism 102. The wire coupling 100 includes a shaft 110 inserted through the shaft holes 60a, 60b, another shaft 112 (perpendicular shaft) inserted through the shaft holes 60b, 60b, and a gear body 114, which is axially and rotatably supported about the shaft 110. The shafts 110 and 112 are fixed by press fitting or welding, for example, with respect to the shaft holes 60a, 60b. The shaft 112 is positioned on the first rotational axis Oy.

The gear body 114 includes a tubular body 116 and a gear 118, which is disposed concentrically on an upper portion of a tubular body 116. The gear 118 comprises a spur gear having a diameter greater than that of the tubular body 116.

Figure 4:
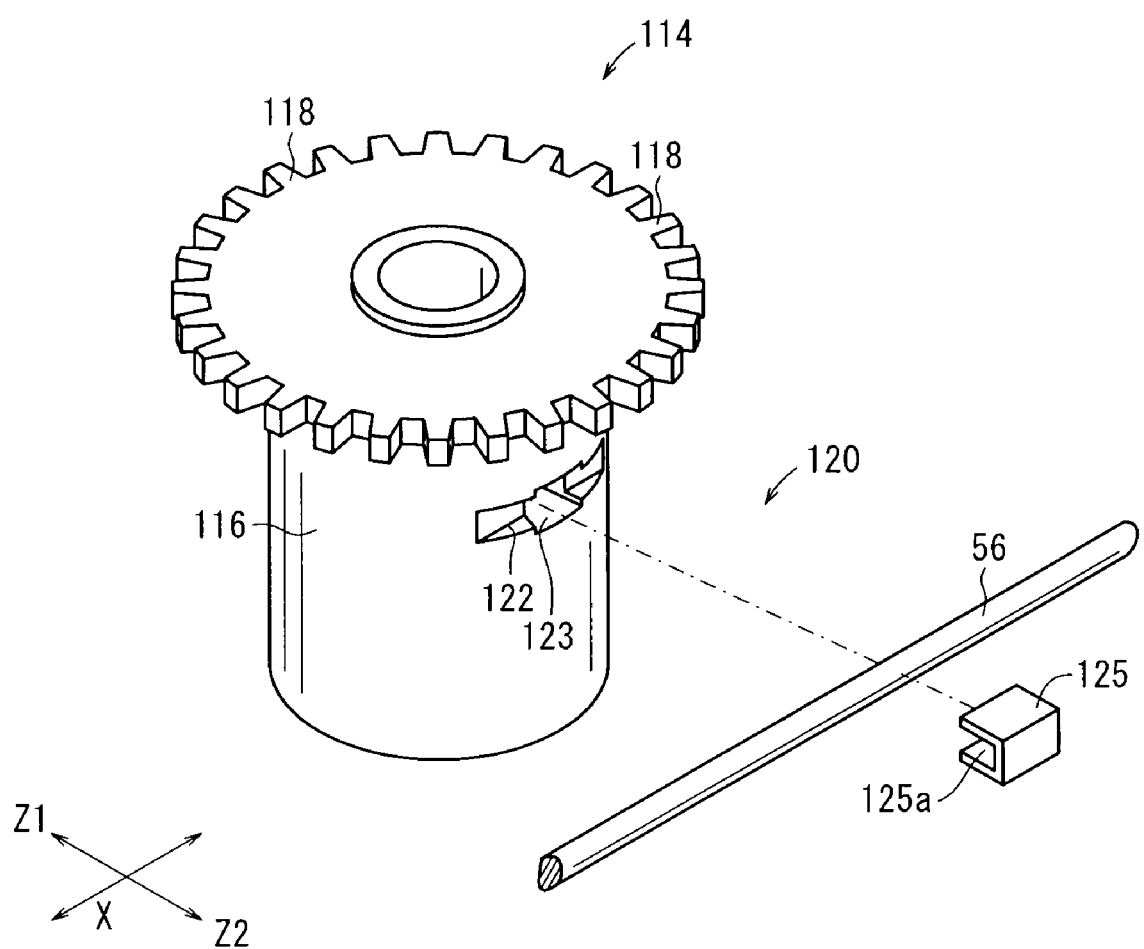
FIG. 4 is an exploded perspective view of a wire fixing mechanism.

As shown in FIG. 4, a wire fixing mechanism 120 is disposed in the tubular body (rotating body) 116. The wire fixing mechanism 120 includes a groove 122 that extends laterally (in the X direction at a neutral posture) at a slightly upward portion on the Z2 direction side of the tubular body 116, and a fixing member 125, which is inserted and fixed in the center of the groove 122. A recess 123 in which the fixing member 125 is inserted and fixed is disposed in a center portion of the groove 122. The orientation of the groove 122 may be slightly inclined, if desired, so as to conform to a helical shaped winding of the wire 56.

The width and maximum depth of the groove 122 are set roughly equivalently to the diameter of the wire 56. The shape of the recess 123 is rectangular as viewed from a side surface thereof, and as viewed in cross section (see FIG. 5), the upper and lower surfaces thereof narrow toward the back portion of the recess 123, and are joined in an arcuate shape with respect to the bottom surface 123a thereof.

The fixing member 125 initially surrounds three sides of the wire 56 as viewed in cross section, and both end pieces 125a thereof are formed with shapes that project beyond the surface of the wire 56. The fixing member 125 can be manufactured inexpensively by press forming, for example.

The fixing member 125 has a squared U-shape in cross section, so that the flat surface thereof can easily be pressed by a tool, thereby enabling the fixing member 125 to be inserted easily into the recess 123. With a rounded U-shape, the inner side surface of the fixing member 125 can easily abut against the wire and the wire can be reliably retained by the fixing member 125. Preferably, a backend portion of the inner side surface of the fixing member 125 is semicircular in cross section, whereas the outer side end portion thereof has a flat surface.

Figure 5:
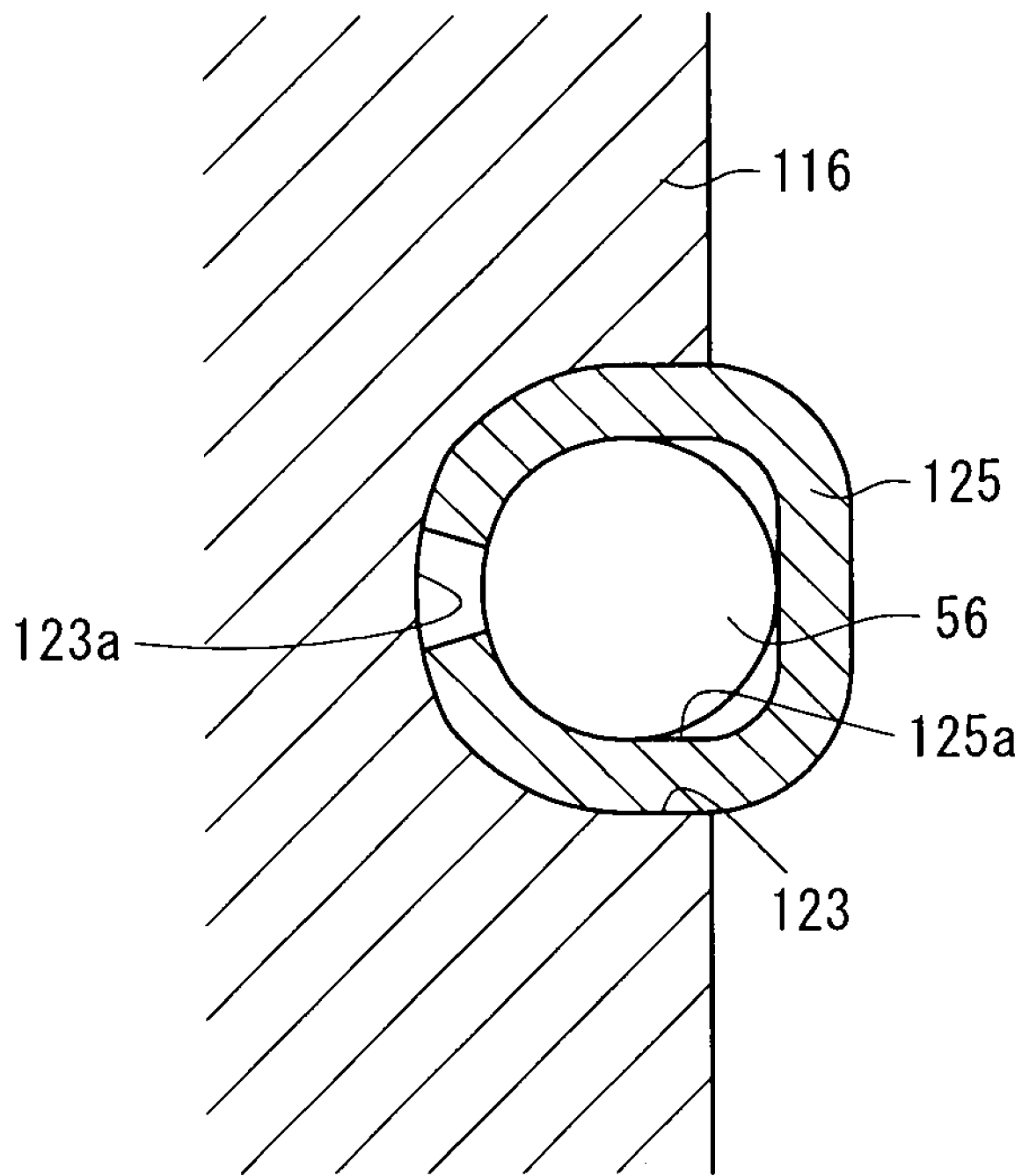
FIG. 5 is a cross sectional side view of the wire fixing mechanism.

As shown in FIG. 5, the projecting portions of the end pieces 125a of the fixing member 125 are inserted into the recess 123 and approach each other, whereby the wire 56 can be pressed and fitted into the recess 123. Stated otherwise, the end pieces 125a of the fixing member 125 are displaced along the wall surfaces of the recess 123, so that the wire 56 can be affixed, as though affixed by stapling.

Further, the fixing member 125 is mounted with respect to the wire 56 from a side thereof and can be inserted into the recess 123. Therefore, there is no difficulty, such as the fixing member 125 passing from an end of the wire 56, so that the wire 56 can easily be affixed. By inserting the fixing member 125 into the recess 123, portions of the wire 56 are fitted into the groove 122, and the wire 56 is affixed with respect to the tubular body 116 while the orientation thereof is regulated horizontally.

Figure 6:
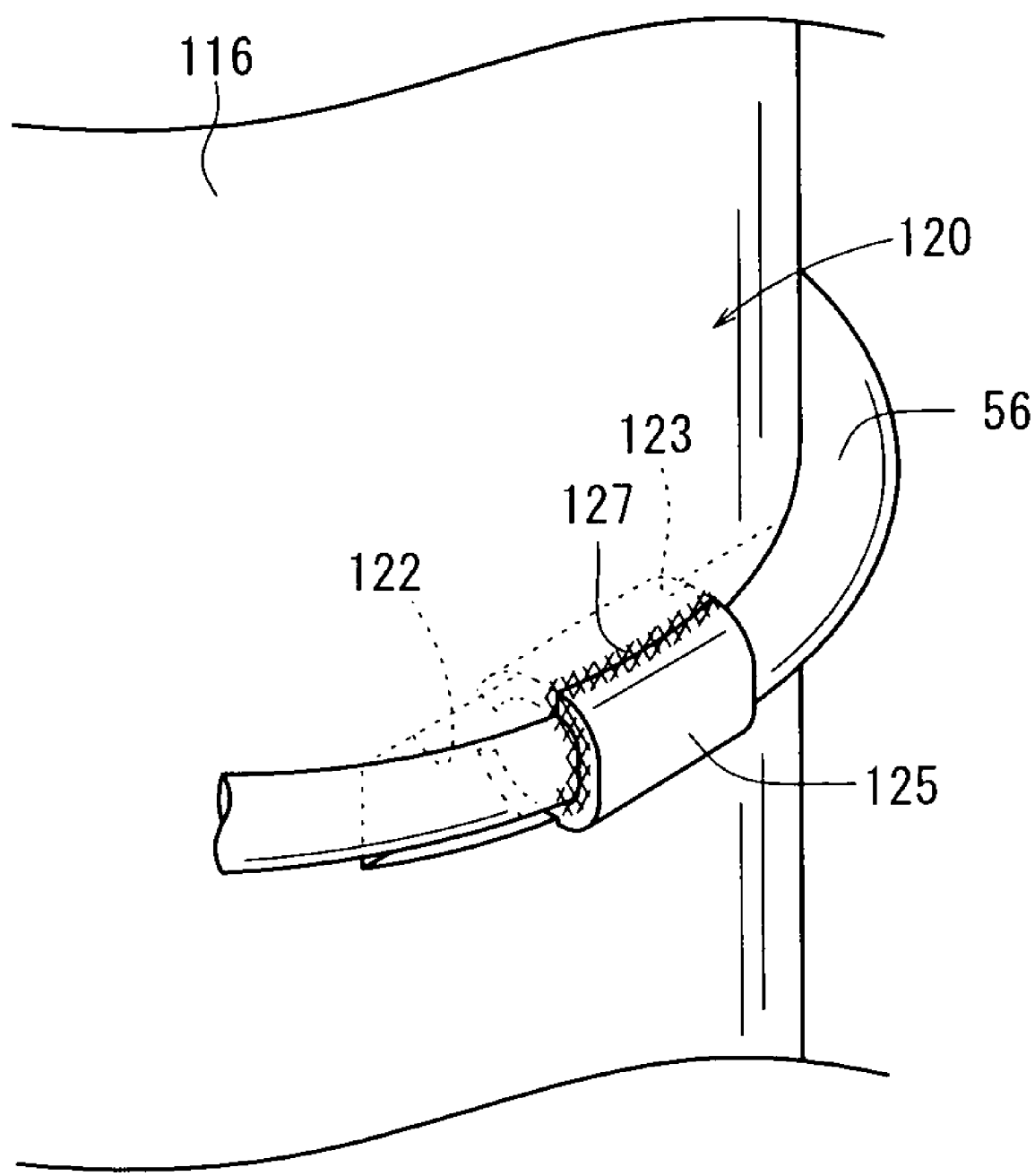
FIG. 6 is a perspective view of a wire fixing mechanism in which welding is used concomitantly therewith.

As shown in FIG. 6, after the fixing member 125 is inserted into the recess 123, if the fixing member 125 and the tubular body 116 are affixed by welding, the wire 56 can be more securely affixed with respect to the tubular body 116, and power (motive force) can be more reliably transmitted thereby. The portion 127 shown by hatching in FIG. 6 shows a welding location. Welding may be carried out by welding at a single location, multi-spot welding, or by welding around the entire periphery of the fixing member 125. Concerning the type of welding used, various methods, for example, laser welding, can be employed.

Figure 7:
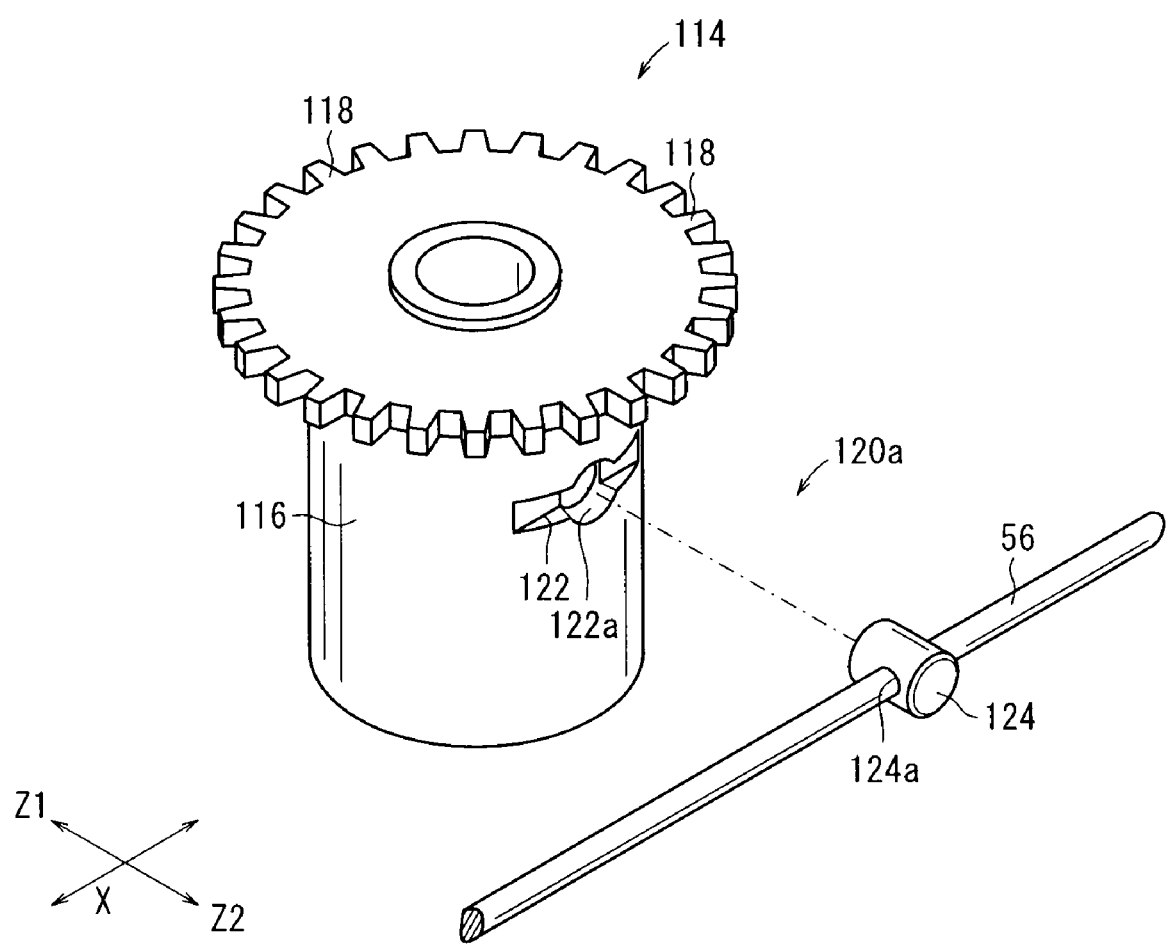
FIG. 7 is an exploded perspective view of a wire fixing mechanism according to a variant example.
Figure 8:
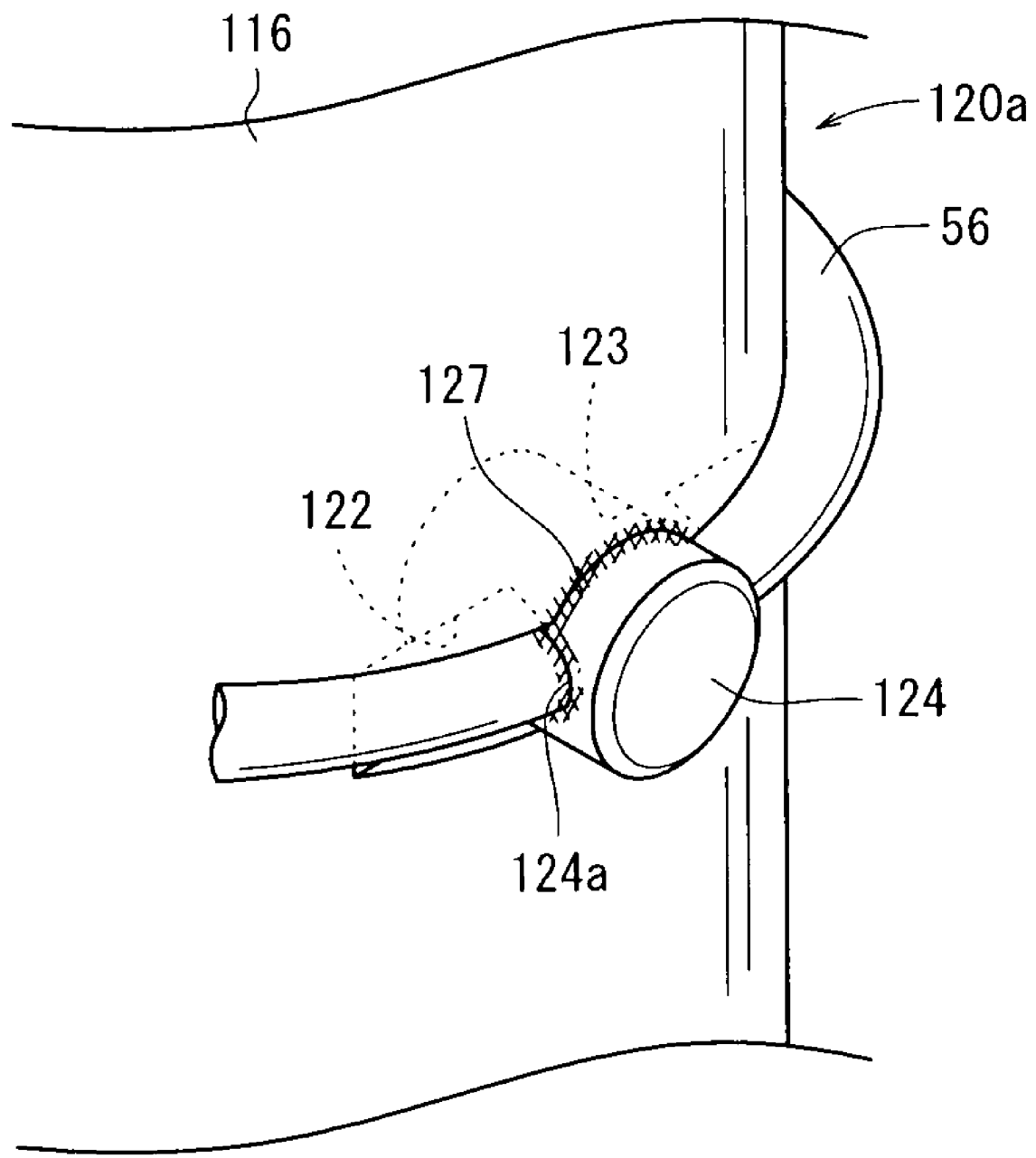
FIG. 8 is a perspective view of the wire fixing mechanism according to the variant example.

As shown in FIGS. 7 and 8, as a variant example of the wire fixing mechanism 120, a wire fixing mechanism 120a includes a cylindrically shaped fixing pin (fixing member) 124 having a constant diameter, which is disposed in the center of the groove 122. A recess 122a into which the fixing pin 124 is inserted and fixed, is disposed in a central portion of the groove 122. A hole 124a through which the wire 56 is capable of penetrating, is formed in the fixing pin 124 and passes laterally through the fixing pin 124. The wire 56 is passed through the hole 124a, and by inserting the fixing pin 124 into the recess 122a, a portion of the wire is fitted in the groove 122, and the wire 56 is affixed with respect to the tubular body 116 while the orientation thereof is regulated horizontally. Thereafter, as shown in FIG. 8, the fixing pin 124 and the wire 56 can be affixed reliably with respect to the tubular body 116 by welding (laser welding or the like).

With the wire fixing mechanism 120a according to this variant example, by providing the recess 122a having a constant diameter cylindrical shape in the tubular body 116, and by utilizing the fixing pin 124 which is fitted into the recess 122a, the wire is securely positioned with respect to the tubular body 116. In this case, the wire 56 may also be welded to at least one of the fixing pin 124 and the tubular body 116.

Returning to FIG. 3, the compound mechanism 102 is a mechanism that serves both to open and close the end effector 104, as well as to, in combination therewith, cause a change in the posture of the end effector 104.

The compound mechanism 102 includes a gear body 126, a main axis member 128, and a gear body 130, which are rotatably supported on the shaft 112, and which are arranged in this order from the Y1 direction toward the Y2 direction. The wires 52 and 54 are affixed in a similar manner.

The gear body 126 includes a tubular body 132, and a gear 134 disposed concentrically on an upper portion of the tubular body 132. The gear 134 is of the same thickness as the gear 118 and is disposed so as to mesh with the gear 118.

The gear body 130 is essentially identical in shape to the gear body 126, but is in an upside-down orientation with respect to the gear body 126. The gear body 130 comprises a tubular body 136 and a gear 138 disposed concentrically on a lower portion of the tubular body 136. The tubular body 136 is substantially identical in diameter and shape to the tubular body 132. The gear 138 has a number of teeth, which may be somewhat smaller than that of the teeth of the gear 134. A wire fixing mechanism 120, which is similar to the wire fixing mechanism 120 of the tubular body 116, is disposed on a side surface of the tubular body 136 that faces the Z2 direction, such that the wire 54 is fastened to the tubular body 136 thereby.

On a side surface in the Z2 direction of a given tubular body on the main axis member 128, a wire fixing mechanism 120 similar to that of the tubular body 116 is provided, and the wire 52 is affixed therein.

The main axis member 128 is rotated in yawing directions about the first rotational axis Oy accompanying reciprocating movement of the wire 52, whereby the support bar can make swinging movements in the XZ plane.

The compound mechanism 102 includes mechanisms, which drive opening and closing of the end effector 104 as well as to perform driving in the rolling direction, and a cover 160 for covering such mechanisms.

The cover 160 serves to protect the respective components of the compound mechanism 102 and the end effector 104. The cover 160 includes a tubular portion 180 extending in the Z2 direction, and a pair of ears 182, which project in the Z1 direction from left and right sides of the tubular portion 180. The ears 182 have shapes such that circumferential wall portions of the tubular portion 180 extend in the Z1 direction, in gradually tapering conical shapes. The cover 160 has a lower portion fastened to a portion of the end effector 104 by a cover-fastening pin. The cover 160 has a diameter, which is equal to or smaller than the diameter of the connecting shaft 48 when viewed in front elevation.

The cover 160 may be in the form of a hollow cylindrical or conical-shaped cover for covering the compound mechanism 102 and the end effector 104, almost in their entirety, to such an extent that operations of the compound mechanism 102 and the end effector 104 will not be hampered. Further, the cover 160 may also be fastened using the pin.

By means of such a cover 160, foreign matter (body tissues, medical agents, sutures, etc.) can be prevented from entering inside the compound mechanism 102 and the end effector 104 making up the working unit.

Next, the structure and operation of the connector 15 in the working unit 16 shall be explained with reference to FIGS. 9 through 13. In the following explanatory views, to facilitate understanding of the structure of the connector 15, a condition is shown in which the cover 37 (see FIG. 1) has been removed therefrom.

Figure 9:
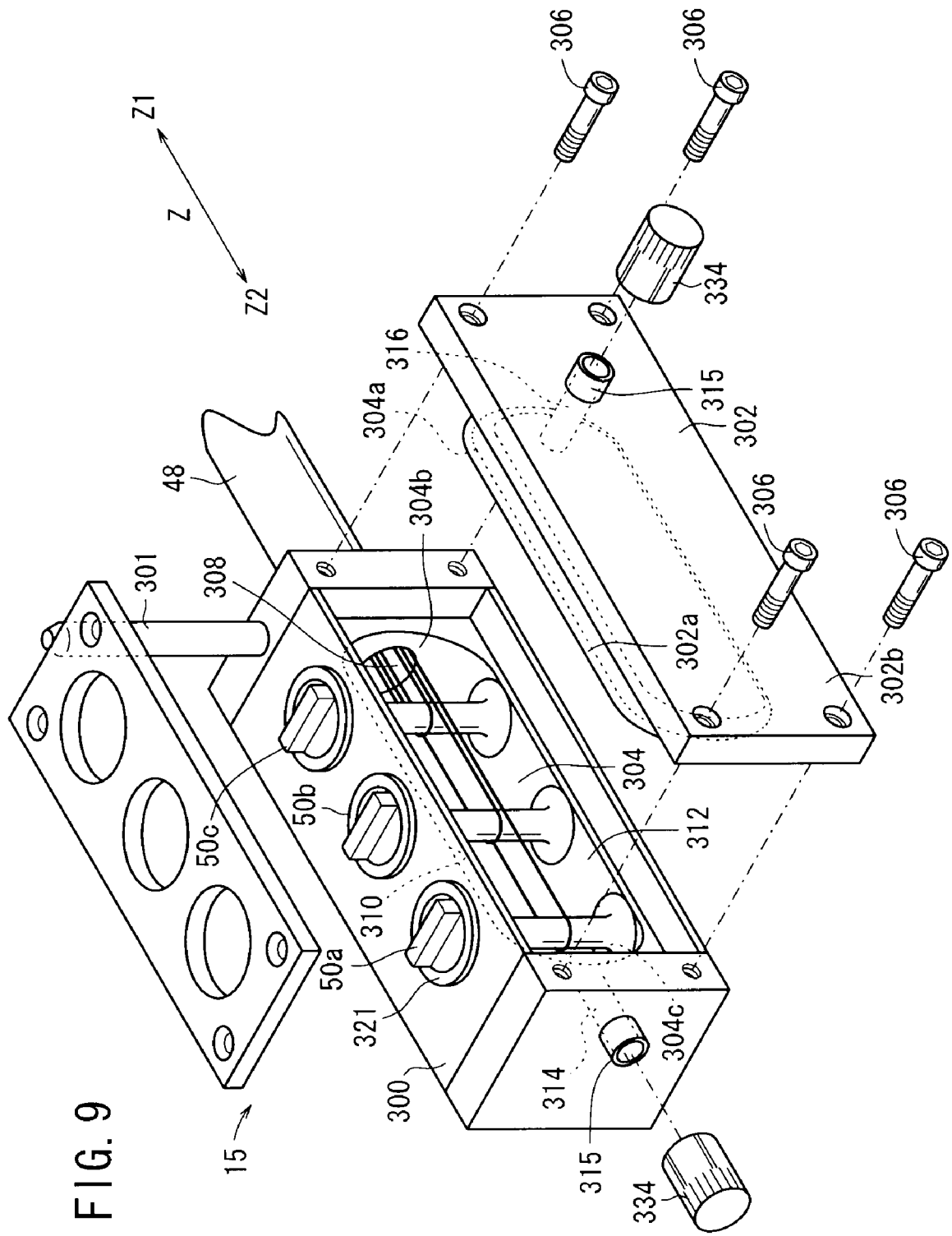
FIG. 9 is an exploded perspective view of a connector used for connecting the working unit with respect to the operation command unit.

As shown in FIG. 9, the connector 15 includes a connector main body 300 and a cover 302 for covering a side thereof. An upwardly projecting electrical terminal post 301 is formed on an upper surface of the connector main body 300. By applying a specified voltage to the electrical terminal post 301, electrical power can be supplied to a predetermined member (e.g., a chip used for energizing an electrical knife) of the distal end working unit 12.

Figure 10:
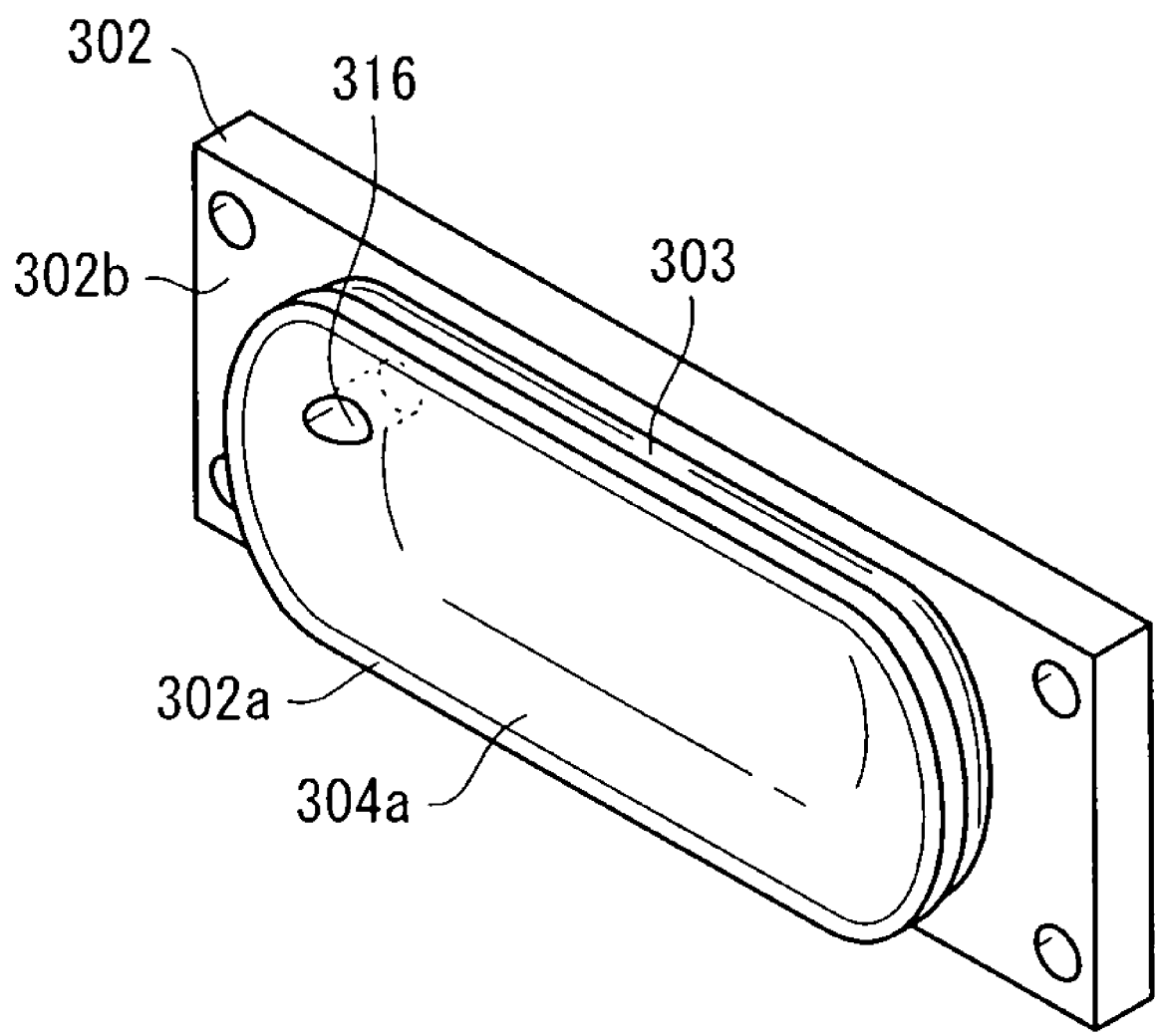
FIG. 10 is a perspective view of a cover of the connector.

As shown in FIG. 10, the cover 302 includes a thin columnar portion 302a, which is shaped arcuately on both ends thereof, and a rectangular plate member 302b, which is connected to an end of the columnar portion 302a. A recess (interior cavity) 304a is provided on an inner side surface of the columnar portion 302a. An annular groove is disposed around an outer periphery of a joined location between the columnar portion 302a and the plate member 302b, with an o-ring 303 being disposed in the annular groove.

As shown in FIG. 9, the cover 302 is affixed to the connector main body 300 by a plurality of screws 306. The connector main body 300 comprises an interior cavity 304 therein, which is equipped with an inner surface thereof that adjoins together smoothly with the recess 304a (see FIG. 12). In the following descriptions, the interior cavity 304 shall be assumed to include the recess 304a therewith. The connector 15 may be constructed, for example, from resin or metallic materials.

The connector 15 and the interior cavity 304 thereof have a longitudinal dimension along the axial direction of the connecting shaft 48 (in other words, in the Z direction), and pulleys 50a, 50b, 50c, which are supported rotatably, are aligned along the longitudinal direction of the connector 15. Wires 52, 54, 56, which are wound around the pulleys 50a to 50c, pass through an opening 308 and extend respectively in the Z1 direction.

The interior cavity 304 includes the aforementioned opening 308 that communicates with the connecting shaft 48, which is disposed at the Z1 direction end, a flat top surface 310 and bottom surface 312, and a first cleaning hole 314 and a second cleaning hole 316. Nipples 315 are provided on the first and second cleaning holes 314, 316 to facilitate attachment of a tube 320 (see FIG. 12) thereto. When cleaning is not being carried out, the respective nipples 315 may be blocked by insulating plugs 334 (see FIG. 9). The insulating plugs 334 may be affixed, for example, by screw-fitting.

By means of the insulating plugs 334, the locations to which voltages are applied through the electrical terminal post 301 can be prevented from being exposed to the outside, and an airtight condition of the interior cavity 304 can be maintained. Because the nipples 315 project toward the outside, insulation can be obtained merely by providing the insulating plugs 334 thereon. The cover 37 (see FIG. 1) may also operate to provide insulation.

Figure 11:
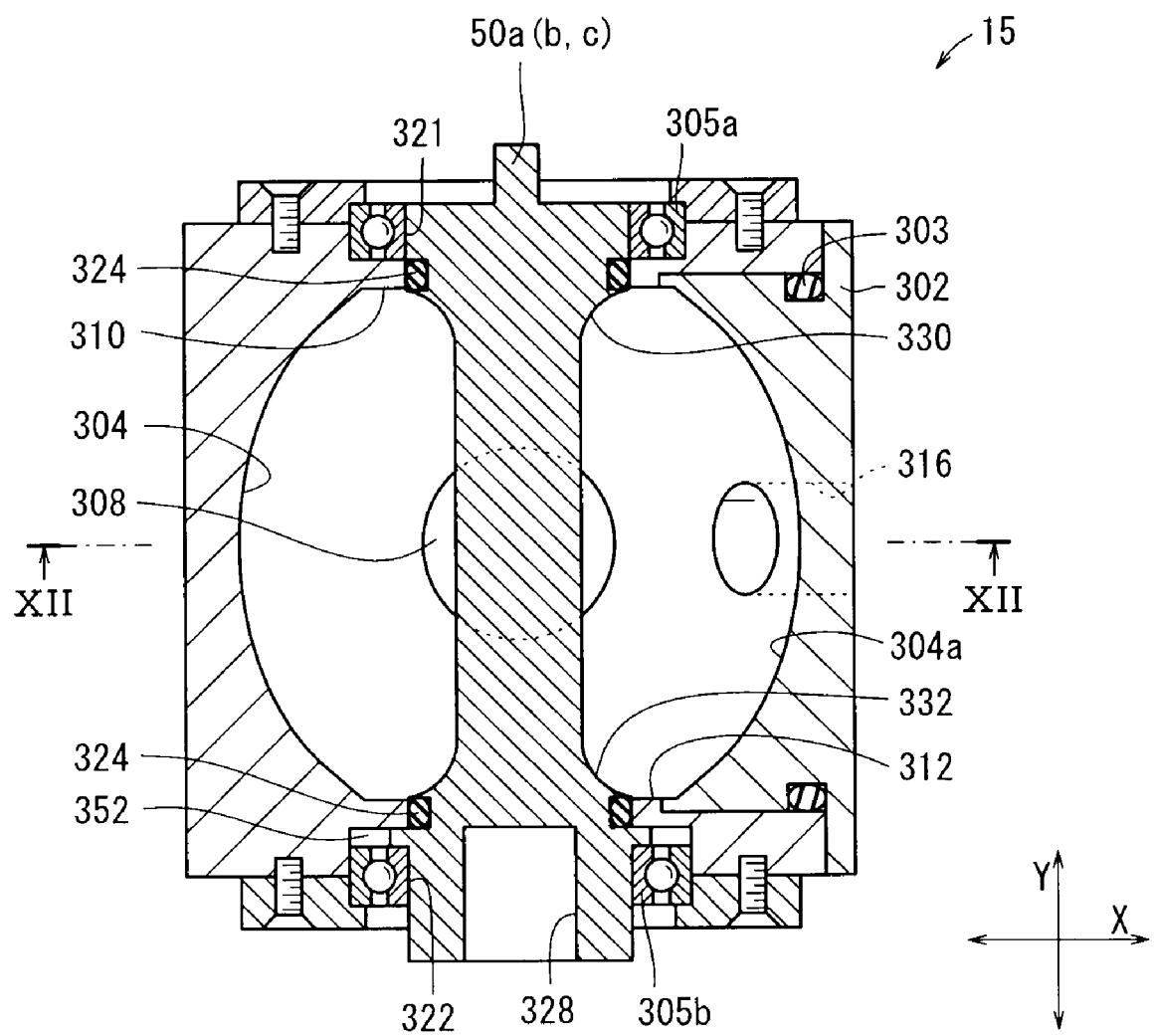
FIG. 11 is a cross sectional rear view of the connector for connecting the working unit with respect to the operation command unit.

Further, as shown in FIG. 11, the interior cavity 304, as viewed in the XY plane cross section (i.e., a cross section perpendicular to the longitudinal direction), also has arcuate shaped left and right surfaces, apart from the top surface 310 and the bottom surface 312, which are smoothly joined with respect to the top surface 310 and the bottom surface 312, so that in the XY cross section the interior cavity 304 is configured overall with a roughly circular shape. In this manner, in the XY cross section, the interior cavity 304 is devoid of angles, and thus, accumulation of foreign matter thereon, and contamination of the interior cavity 304, is made difficult.

Figure 12:
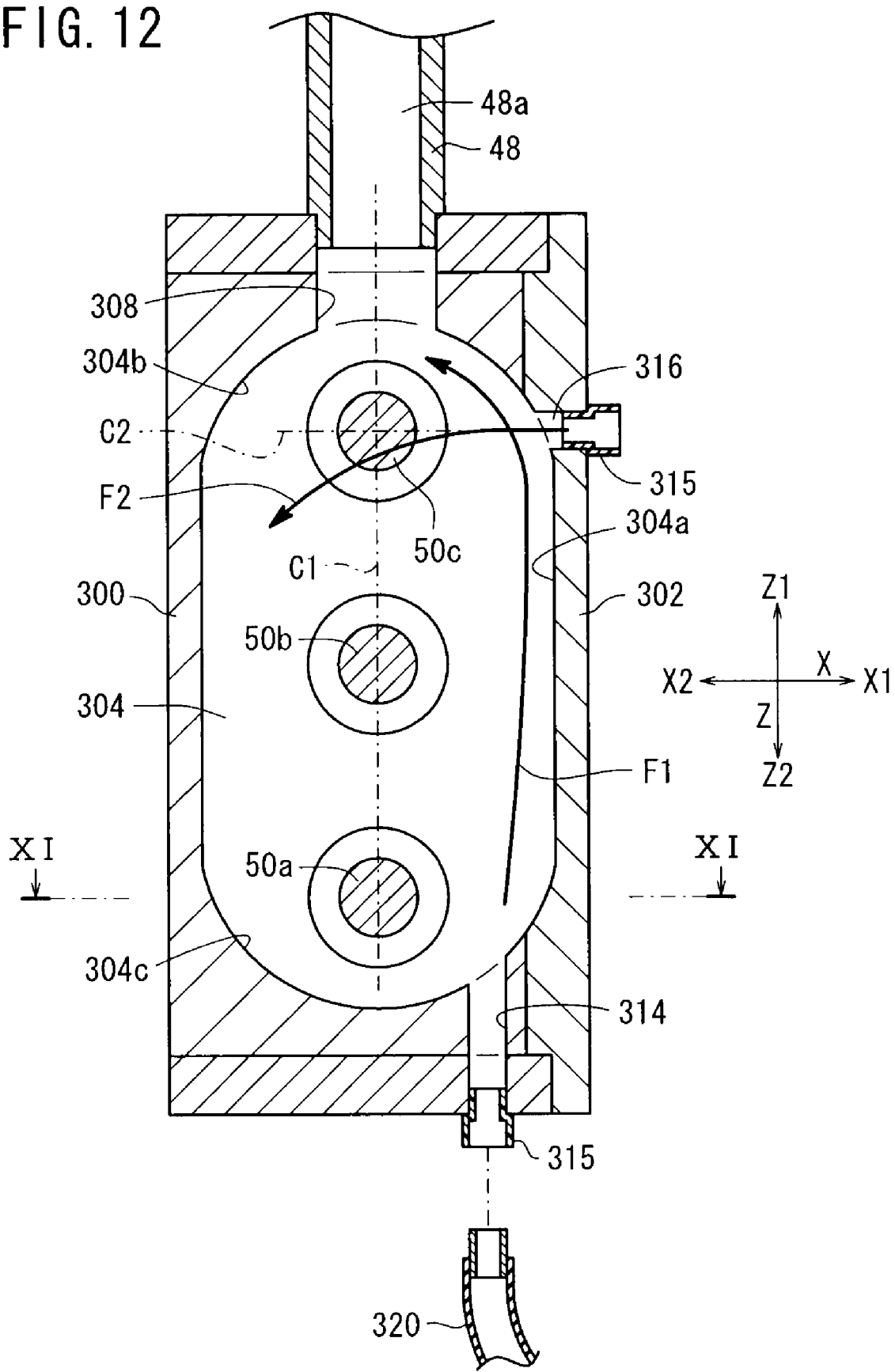
FIG. 12 is a cross sectional plan view of the connector for connecting the working unit with respect to the operation command unit.

Still further, as shown in FIG. 12, the interior cavity 304 has a roughly hemispherical shape at the end portions 304b and 304c thereof in the Z1 and Z2 directions. In other words, in the XZ cross section as well, the interior cavity 304 is devoid of angles, and thus, accumulation of foreign matter thereon, and contamination of the interior cavity 304, is made difficult.

Further, in accordance with the above-described shape of the interior cavity 304, there are no locations where the cleaning agent tends to accumulate, and thus the cleaning agent flows easily. In addition, the cleaning agent does not unevenly flow only at any given location, and thus, the cleaning agent easily comes into contact with the overall surface of the interior cavity 304.

Returning now to FIG. 11, the pulleys 50a to 50c are inserted into supporting holes 321 and 322 provided in the top surface 310 and bottom surface 312, and are axially supported by upper and lower bearings 305a, 305b. The pulleys 50a to 50c are sealed by o-rings (annular seals) 324, which are disposed respectively on the top surface 310 and the bottom surface 312. Engagement holes 328, in which the rotational shafts of the motors 40, 42, 44 engage, are provided on the lower surface of each of the pulleys 50a to 50c. With the exception of the opening 308, the interior cavity 304 has a hermetically sealed construction provided by means of the o-ring 303 and the o-rings 324. Therefore, during surgery, leakage of gases (carbon dioxide, etc.) from the body cavity of the patient through the working unit 16 is prevented, and the internal pressure inside the body cavity can be kept at a stable value.

The upper and lower end portions 330, 332 of the pulleys 50a to 50c inside the interior cavity 304 have trumpet-like formations, which expand in diameter toward the top surface 310 and bottom surface 312, adjoining smoothly with respect to the top surface 310 and bottom surface 312. In this manner, because the end portions 330, 332 have shapes that expand in diameter toward the top surface 310 and bottom surface 312, angles are not formed at the adjoining locations thereof with the top surface 310 and bottom surface 312, and thus, accumulation of foreign matters on the end portions is difficult and unlikely to occur, and contamination thereof is made difficult. Further, a sufficient amount of cleaning agent comes into contact around the end portions 330 and 332, whereby the cleaning effect is enhanced. The end portions 330, 332 do not have to be trumpet shaped exclusively and, for example, may be conically shaped as well.

The first cleaning hole 314 and the second cleaning hole 316 provide holes through which a cleaning agent (including compressed air or the like) flows (i.e., is infused and outfused). The cleaning holes 314, 316 can be connected to a tube 320 (see FIG. 12) that enables the cleaning agent to flow therethrough.

Figure 14:
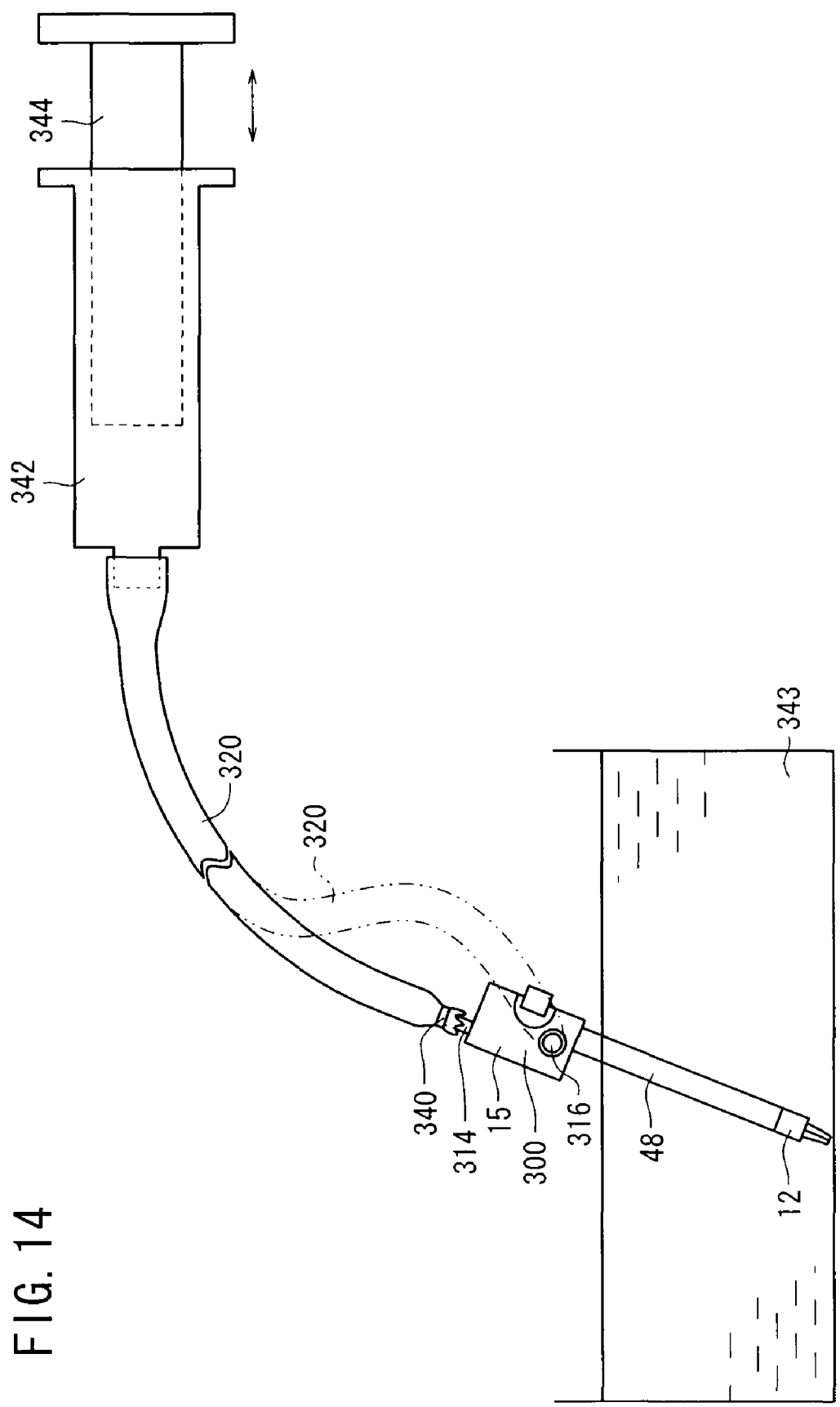
FIG. 14 is an explanatory drawing showing an aspect of cleaning the working unit by a first cleaning method according to an embodiment of the present invention.

As a result of the cleaning agent being caused to flow from the first cleaning hole 314 and the second cleaning hole 316, the interior cavity 304 and the pulleys 50a, 50b, 50c making up driven rotating bodies can easily be cleaned. In the cleaning method as shown in FIG. 14, the first cleaning hole 314 and the second cleaning hole 316 also function both as a suction inlet and a discharge outlet for the cleaning agent.

As made clear from FIG. 12, the first cleaning hole 314 is disposed at a position that is offset slightly in the X1 direction from a parallel axis C1 along which the pulleys 50a, 50b and 50c are arrayed in parallel. Accordingly, the cleaning agent, which is infused from the first cleaning hole 314, does not impinge directly against the pulleys 50a, 50b, 50c, but as shown by the arrow F1, flows from the side surface in the X1 direction toward the end portion 304b of the Z1 direction, generating a counterclockwise-directed rotational flow inside the interior cavity 304, whereby cleaning of the interior cavity 304 can be effectively carried out. Further, owing to such a rotational flow, effective cleaning of the pulleys 50a, 50b, 50c can also be carried out.

The first cleaning hole 314 is positioned at one end on a side (i.e., the Z2 side) opposite from the side on which the connecting shaft 48 is connected. Owing thereto, the cleaning agent infused from the first cleaning hole 314 flows easily into the interior cavity 304, passing through the opening 308 and reaching to the connecting shaft 48 and the distal end working unit 12, whereby cleaning of such locations can effectively be carried out.

Moreover, as understood more clearly from FIG. 12, owing to the fact that the first cleaning hole 314 and the opening 308 are disposed, respectively, at an end of the end portion 304c and at the center of the end portion 304b, after the cleaning agent has been infused, the cleaning agent impinges against an end of the end portion 304b, generating an appropriate turbulence therein and resulting in a turbulent flow, which enhances the cleaning effect.

The second cleaning hole 316 is disposed on a surface in the X1 direction within the interior cavity 304, and opens in the vicinity of a side thereof to which the connecting shaft 48 is connected (i.e., on the Z1 side), and further is disposed along a direction C2 directed toward the pulley 50c. In the vicinity of the opening 308 where the connecting shaft 48 is connected, and in particular at the end portions 330 and 332 of the pulley 50c, there is a tendency for contamination to occur more easily as a result of body fluid, etc., passing and coming in through the connecting shaft 48. However, owing to the fact that the second cleaning hole 316 is disposed in the vicinity of the center of the pulley 50c in the interior cavity 304, such locations can be cleaned intensively and with special emphasis. Further, the cleaning agent directly impinges on the pulley 50c from a nearby distance, and therefore the pulley 50c can be cleaned more intensively.

The cleaning agent infused from the second cleaning hole 316, after impinging directly on the pulley 50c, flows in a counterclockwise direction inside the interior cavity 304, as shown by the arrow F2, along the side surface in the X2 direction, so that cleaning of the interior cavity 304 can be carried out thereby.

Incidentally, as shown by the arrow F1, since the cleaning agent infused from the first cleaning hole 314 also flows in a counterclockwise direction, the flow does not cause a backlash against the cleaning agent introduced from the second cleaning hole 316. Stated otherwise, because the first cleaning hole 314 is disposed at one end in the Z2 direction, whereas the second cleaning hole 316 is disposed at the other end in the Z1 direction, and since both of the cleaning holes 314, 316 are disposed respectively at positions shifted in the X1 direction from the parallel axis C1 (i.e., the axis C1 along which the pulleys 50a to 50c are arrayed in parallel), and moreover, since the cleaning holes 314, 316 open at orientations differing substantially 90 degrees from each other, the cleaning agent which is infused respectively therefrom flows cooperatively along the same direction, so that cleaning of the interior cavity 304 can be carried out synergistically. Accordingly, infusion of the cleaning agent from the first cleaning hole 314 and the second cleaning hole 316 can be performed simultaneously.

It is a matter of course that the cover 302 may be removed, and cleaning of the cover 302 and the connector main body 300 can be carried out separately.

In FIGS. 11 and 12, in order to facilitate understanding of the shapes of the interior cavity 304 and the pulleys 50a to 50c, the wires 52, 54, 56 are omitted from illustration.

Figure 13:
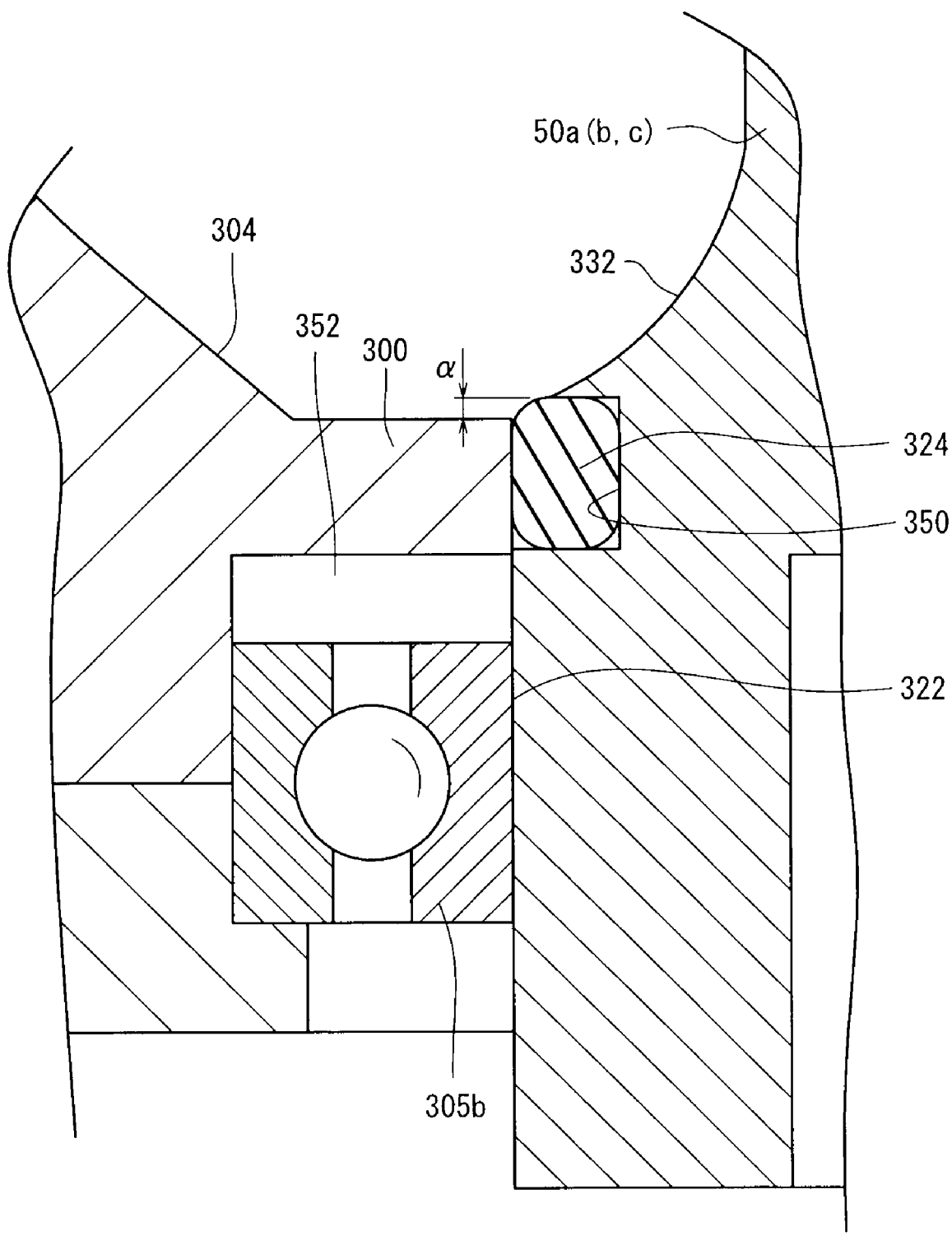
FIG. 13 is an enlarged cross sectional rear view of a portion of the connector for connecting the working unit with respect to the operation command unit.

As shown in FIG. 13, annular grooves 350 are provided, which surround portions of the pulleys 50a to 50c that are inserted into the supporting holes 322 of the interior cavity 304, with o-rings 324 being disposed in the annular grooves 350. The annular groove 350 is disposed in the vicinity of an upper end of the supporting hole 322, whereby the upper end of the annular groove 350 is exposed in the interior cavity 304. In other words, the annular groove 350 projects toward an inner side from a bottom surface of the interior cavity 304, by a minute dimension α, as shown in FIG. 13. Owing thereto, a minute gap 352 between the pulleys 50a to 50c and the supporting holes 322 is blocked completely by the o-ring 324, whereby it becomes difficult for foreign matter to accumulate in the minute gap 352.

Next, a method for cleaning the working unit 16 shall be described with reference to FIGS. 14 and 15.

As shown in FIG. 14, one end of a tube 320 is connected to the first cleaning hole 314 (see FIG. 12) of the connector 15, and the first cleaning hole 314 and the tube 320 are sealed in a fluid-tight manner by a band (sealing means) 340. The sealing means is not limited to the band 340, but may be any means providing a suitable fluidtight condition. Such sealing also is not limited to a means that strictly prevents leakage of the cleaning agent. So long as the cleaning agent can flow through the tube 320, a small amount of leakage can be tolerated. At this time, the second cleaning hole 316 (see FIG. 12) is blocked.

Next, the other end of the tube 320 is connected to a syringe (suction and discharge means) 342, and an end of the connecting shaft 48, i.e., the distal end working unit 12, is immersed in the cleaning agent (which may be a water or an enzyme cleaning agent, for example), which is provided in a moderately-large vat 343. Initially, it is preferable to operate the piston 344 of the syringe 342 until the syringe 342 becomes filled with the cleaning agent. Preferably, the syringe 342 is chosen to have a sufficiently large capacity, which is greater than the total interior volume of the connecting shaft 48 and the tube 320.

Next, by reciprocally moving the piston 344, the cleaning agent is repeatedly sucked and discharged from the distal end working unit 12. The cleaning agent is drawn in from the distal end working unit 12 and passes into the hollow space 48a of the connecting shaft 48, reaching the first cleaning hole 314. The cleaning agent that has passed through the first cleaning hole 314 passes through the tube 320 and is drawn into the syringe 342. When the fluid is discharged, the fluid flows in reverse and passes from the syringe 342, through the tube 320, the first cleaning hole 314, the connecting shaft 48 and the distal end working unit 12, whereupon the cleaning agent is discharged into the vat 343. The discharged cleaning agent is diluted with the remaining cleaning agent in the vat 343, so that when sucked again in the next cycle, a cleaning agent having adequate purity can be drawn in.

In accordance with such a cleaning method, by the continual reciprocating movements of the piston 344 in the syringe 342, the cleaning agent is sucked and discharged through the hollow space 48a of the connecting shaft 48, whereby the connecting shaft 48 and the connector 15 can be cleaned easily and highly effectively at the same time.

As shown by the imaginary lines in FIG. 14, in place of the first cleaning hole 314, the tube 320 may also be connected to the second cleaning hole 316 for carrying out cleaning. In this case, the first cleaning hole 314 is blocked instead of the second cleaning hole 316.

Further, a bifurcated or forked tube 320 may be used, wherein cleaning is carried out by connecting the tube 320 to both the first cleaning hole 314 and the second cleaning hole 316.

Figure 15:
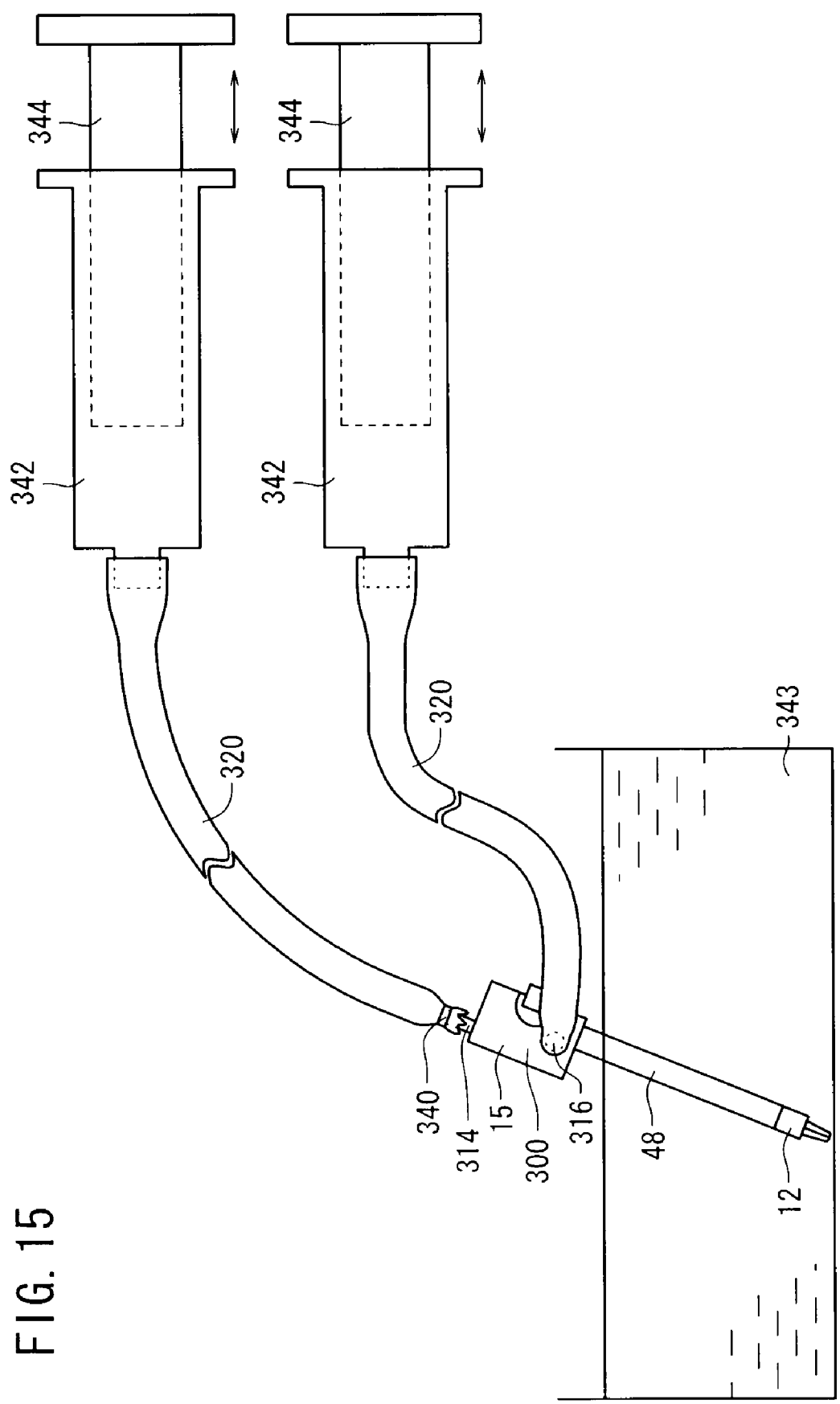
FIG. 15 is a explanatory drawing showing an aspect of cleaning the working unit by a second cleaning method according to an embodiment of the present invention.

Still further, as shown in FIG. 15, two syringes 342 may be provided and connected independently with respect to the first cleaning hole 314 and the second cleaning hole 316. In this case, the two pistons 344 may be moved simultaneously at the same phase, each of the pistons 344 may be moved alternately, the pistons 344 may be moved at the same or at different speeds, or the pistons 344 may be moved in a composite manner.

Further, even in the case that a structure is provided in which the piston 344 is operated automatically to be reciprocally moved over a long period of time, only the cleaning agent provided in the vat 343 is utilized, so that a large amount of cleaning agent is not consumed inadvertently. The used cleaning agent is collected into the vat 343 without scattering or spillage of the cleaning agent, so that no special anti-scattering means or collecting means is required, and disposal processing of the cleaning agent can be easily performed. The fluid suction and discharge means is not limited to the syringe 342. For example, an automatically driven cylinder or the like may be used in place of the syringe 342.

As described above, with the manipulator 10 according to the present invention, by allowing the cleaning agent to flow through the first cleaning hole 314 and the second cleaning hole 316, the interior cavity 304 of the connector 15 can easily be cleaned.

Furthermore, by insertion of both end pieces 125a of the fixing member 125 into the recess 123 of the tubular body 116, the both end pieces 125a approach each other, whereby the wire 56 is pressed and fixed on the tubular body 116. As a result, the wire 56 can be easily and reliably affixed with respect to the tubular body 116.

The manipulator 10 has been described as pertaining to applications for medical uses wherein the manipulator 10 is handled and operated directly by an operator. However, the intended use thereof is not necessarily limited to such uses. For example, the invention may be applied to a remote operation mechanism for performing techniques through an electronic communications means or the like, at a location separated from the patient.

The working unit 16 has been described as being connected to an operation command unit 14, which is operated manually. However, as shown in FIG. 16, the working unit 16 may also be applied to a surgical robot system 700.

The surgical robot system 700 includes a multi-articulated robot arm 702 together with a console 704. The working unit 16 is connected to an end of the robot arm 702. The same mechanism as that of the aforementioned actuator block 30 is provided at the end of the robot arm 702, thereby enabling connection and driving of the working unit 16. In this case, the manipulator 10 is made up from the robot arm 702 and the working unit 16. The robot arm 702 may comprise means therein for causing movements of the working unit 16, and is not limited to a stationary system, but for example, may also be an autonomous mobile system. For the console 704, a table type structure or a control panel structure may be adopted.

When the robot arm 702 includes six or more independent joints (rotational or slide axes), the position and orientation of the working unit 16 can be set arbitrarily in an appropriate manner. An end actuator block 30 may be constructed integrally with an end portion 708 of the robot arm 702.

The robot arm 702 is moved under operations of the console 704, and may be configured to move automatically according to a given program, or to move correspondingly to movements of a joystick 706 disposed on the console 704, or by a combination of such operations. The console 704 includes the functions of the aforementioned controller 45.

Two joysticks 706 and a monitor 710 are provided on the console 704, serving as an operation command section for mechanisms among those of the aforementioned operation command unit 14 excluding the actuator block 30. Although not shown by the present illustration, two robot arms 702 may be provided, which are operated separately by the two joysticks 706. The two joysticks 706 are disposed at positions where they can be easily operated by both hands. The monitor 710 displays information of images or the like produced by an endoscope.

The joysticks 706 are capable of being moved up and down, left and right, and of making twisting or torsional movements, as well as tilting movements, wherein the robot arm 702 can be moved responsive to the movements of the joysticks 706. Further, by the trigger lever 32, the first command lever 34, and the second command lever 36 which are provided on the grip handle 26, the same operations as with the operation command unit 14 are possible.

The joysticks 706 may also comprise a master arm. The communication means between the robot arm 702 and the console 704 may consist of wired or wireless communications, communication over a network, or any combination of the same.

The medical manipulator and cleaning method therefor according to the present invention are not limited to the aforementioned embodiments. Various modifications and/or additional structures may be adopted without departing from the scope of the invention as set forth in the appended claims.

What is claimed is:

1. A cleaning method for a medical manipulator, said medical manipulator comprising:
   a drive unit equipped with a rotary actuator; and
   a working unit which is detachable with respect to said drive unit, said working unit comprising a distal end working unit which is operatively connectable to said rotary actuator,
   wherein said working unit further comprises:

a driven rotating body engaged with said rotary actuator at a connection location of said drive unit;

a retaining chamber for rotatably supporting and retaining said driven rotating body; and at least one cleaning hole through which a cleaning agent is made to flow into and through said retaining chamber, the cleaning method comprising the steps of:

detaching said working unit from said drive unit;

connecting and sealing said cleaning hole to one end of a tube;

providing a cleaning agent suction and discharge means on another end of said tube;

immersing an end of a shaft of said medical manipulator into said cleaning agent; and operating said suction and discharge means to repeatedly carry out sucking and discharging of said cleaning agent from the end of said shaft, and thereby causing said cleaning agent to contact and flow through said retaining chamber.

2. The cleaning method for a medical manipulator according to claim 1, wherein said cleaning hole comprises two cleaning holes, one of said cleaning holes being connected to said tube, and the other of said cleaning holes being blocked.

3. The cleaning method for a medical manipulator according to claim 1, wherein said cleaning hole comprises two cleaning holes, and said tube comprises two tubes, which are connected respectively to said two cleaning holes.

* * * * *